(12) United States Patent
Lange

(10) Patent No.: US 9,394,222 B2
(45) Date of Patent: Jul. 19, 2016

(54) PRODUCTION OF METHACRYLIC ACID

(71) Applicant: SHELL OIL COMPANY, Houston, TX (US)

(72) Inventor: Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/759,470

(22) PCT Filed: Jan. 8, 2014

(86) PCT No.: PCT/EP2014/050182
§ 371 (c)(1),
(2) Date: Jul. 7, 2015

(87) PCT Pub. No.: WO2014/108416
PCT Pub. Date: Jul. 17, 2014

(65) Prior Publication Data
US 2015/0353462 A1    Dec. 10, 2015

(30) Foreign Application Priority Data
Jan. 8, 2013 (EP) .................................. 13150521

(51) Int. Cl.
*C07C 51/353* (2006.01)
*C07C 51/235* (2006.01)
*C07C 45/52* (2006.01)

(52) U.S. Cl.
CPC ............... *C07C 51/353* (2013.01); *C07C 45/52* (2013.01); *C07C 51/235* (2013.01)

(58) Field of Classification Search
CPC ....... C07C 51/353; C07C 51/235; C07C 45/52
See application file for complete search history.

(56) References Cited

U.S. PATENT DOCUMENTS

| 4,677,225 | A * | 6/1987 | Niizuma ........... B01J 27/18 560/214 |
| 2005/0277786 | A1 | 12/2005 | Goto et al. |
| 2011/0137077 | A1 | 6/2011 | Teles et al. |

OTHER PUBLICATIONS

Sato, S. et al.; "Vapor-phase Reaction of Polyols Over Copper Catalysts"; Applied Catalysis A: General Elsevier Science; vol. 347, No. 2; pp. 186-191; Sep. 15, 2008, XP023613565.
Ruppert, Agnieszka M., et al.; "Hydrogenolysis Goes Bio: From Carbohydrates and Sugar Alcohols to Platform Chemicals"; Angew. Chem. Int. Ed., vol. 51, No. 11; pp. 2564-2601; Mar. 12, 2012, XP055059768.
Li, N. et al.; Journal of Catalysis; vol. 270; pp. 48-59; 2010.
Lange, J.P.; Green Chemistry; vol. 4; pp. 546-550; 2002.

* cited by examiner

Primary Examiner — Shailendra Kumar

(57) ABSTRACT

The invention relates to a process for producing methacrylic acid, comprising: converting a C3-oxygenate into propanoic acid, wherein said C3-oxygenate is a compound selected from the group consisting of 1-propanol, monopropylene glycol, monohydroxyacetone, 2-hydroxypropanal, glycerol and dihydroxyacetone; and reacting the propanoic acid with formaldehyde or a precursor of formaldehyde into methacrylic acid. Said C3-oxygenate preferably contains 2 oxygen atoms, and most preferably it is monopropylene glycol.

7 Claims, 1 Drawing Sheet

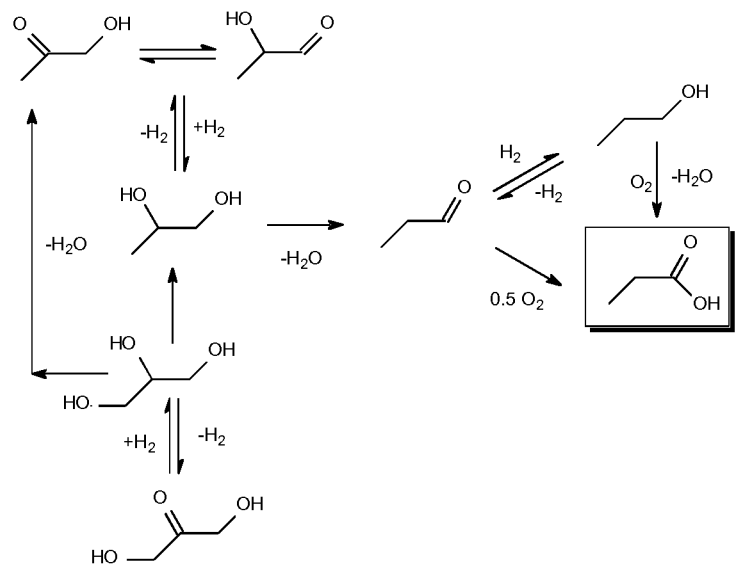

PRODUCTION OF METHACRYLIC ACID

PRIORITY CLAIM

The present application is the National Stage (§371) of International Application No. PCT/EP2014/050182, filed Jan. 8, 1014, which claims priority from European Application No. 13150521.6, filed Jan. 8, 2013 incorporated herein by reference.

FIELD OF THE INVENTION

The present invention relates to a process for producing methacrylic acid.

BACKGROUND OF THE INVENTION

Methacrylic acid is a chemical for which the worldwide demand is high, about 4 Mt/a (million ton per annum) in 2008, which demand is expected to increase significantly. A known route for the production of methacrylic acid and then methyl methacrylate, which is the methyl ester of methacrylic acid, is the reaction of acetone with hydrogen cyanide (HCN) followed by sulfuric acid ($H_2SO_4$) catalysed dehydration and esterification with methanol to methyl methacrylate. The overall reaction stoichiometry for this route is as follows:

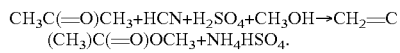

$CH_3C(=O)CH_3+HCN+H_2SO_4+CH_3OH \rightarrow CH_2=C(CH_3)C(=O)OCH_3+NH_4HSO_4.$ A disadvantage of the above-mentioned route for the production of methacrylic acid and its methyl ester is that said route is accompanied by the undesired production of salts, such as above-mentioned ammonium sulfate, in large amounts, as disclosed by J.-P. Lange in Green Chemistry, 2002, 4, p. 546-550.

An alternative route for the production of methacrylic acid is the oxidation of isobutene with an oxygen containing gas. The overall reaction stoichiometry for this route is as follows:

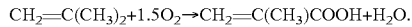

$CH_2=C(CH_3)_2+1.5O_2 \rightarrow CH_2=C(CH_3)COOH+H_2O.$

A disadvantage of the above-mentioned route for the production of methacrylic acid is that two oxygen atoms have to be introduced into the isobutene by the use of an oxygen containing gas at high temperature (about 350° C.) and with release of a large amount of heat (about 600 kJ/mol).

A further disadvantage for both said routes for the production of methacrylic acid is that non-renewable, fossil feedstocks have to be used. Namely, acetone in the first route which acetone may be derived from propene, which propene may be derived from propane. Both propene and propane are currently only readily available as fossil feedstocks and are therefore not renewable. Likewise, in the second route, isobutene has to be used, which isobutene may be derived from isobutane or from crude oil which are also non-renewable, fossil feedstocks.

US 2005/277786 discloses a process for the conversion of propanoic acid to acrylic acid.

S. Sato, et al., Applied Catalysis A: General, 2008. 347(2), 186 teaches a method for conversion of 1,3-propanediol to propanoic acid. However, the same paper teaches that monopropylene glycol is converted mostly to hydroxyacetone under the same conditions, with only a very little propanoic acid formed as a by-product.

In addition to methacrylic acid, monoethylene glycol is also a chemical for which the worldwide demand is high, about 20 Mt/a (million ton per annum) in 2008. Monoethylene glycol may be advantageously produced from sugar sources, such as sucrose, glucose, xylose or fructose and the corresponding polysaccharides, cellulose, hemicellulose, starch and inulin. A disadvantage of this route is that in addition to monoethylene glycol, also a lot of monopropylene glycol is formed. It may even be the case that two to three times more monopropylene glycol is formed than monoethylene glycol. See for example "Hydrogenolysis Goes Bio: From Carbohydrates and Sugar Alcohols to Platform Chemicals" by Agnieszka M. Ruppert et al. in Angew. Chem. Int. Ed., 2012, 51, p. 2564-2601.

In contrast to methacrylic acid and monoethylene glycol, the worldwide demand for monopropylene glycol is not high, about 1.5 Mt/a (million ton per annum) in 2008. Currently, it is estimated that the worldwide demand for monoethylene glycol is ten times higher than that for monopropylene glycol. Because of this lower demand for monopropylene glycol, processes for converting sugar sources into monoethylene glycol may not be commercialized, unless the selectivity to monoethylene glycol would be drastically increased. Such selectivity increase is difficult to achieve. Consequently, there is currently a need in the art to valorize the monopropylene glycol that is automatically formed when transforming sugar sources into monoethylene glycol. A desired valorization could be an application wherein the monopropylene glycol is converted into a chemical for which the worldwide demand is high.

The above-mentioned monopropylene glycol is just one example of a C3-oxygenate. C3-oxygenates contain 3 carbon atoms and 1 or more oxygen atoms. There are also C3-oxygenates other than monopropylene glycol, which may contain 1, 2 or 3 oxygen atoms and which may also be formed as undesired (by)products in certain production processes such as biomass conversion processes. Such biomass conversion process may be the aqueous phase reforming of sugars, as disclosed by N. Li et al. in Journal of Catalysis, 2010, 270, p. 48-59. Examples of such other C3-oxygenates are: 1-propanol, monohydroxyacetone, 2-hydroxypropanal, glycerol and dihydroxyacetone.

Consequently, there is a need in the art to valorize C3-oxygenates in general, such as for example monopropylene glycol or glycerol, which may be formed as undesired (by) products in certain production processes such as biomass conversion processes.

SUMMARY OF THE INVENTION

Surprisingly, it was found that the above-mentioned C3-oxygenates can be valorized by using them in a process for producing methacrylic acid, by first converting them into propanoic acid and then converting the propanoic acid into methacrylic acid. Advantageously, in such way, the C3-oxygenate is converted into a chemical for which the worldwide demand is high, namely methacrylic acid. Further, advantageously, in such way, methacrylic acid may be produced from a renewable feedstock since the starting C3-oxygenates may originate from biomass conversion processes. Further advantages of the present invention appear from the detailed description below.

Accordingly, the present invention relates to a process for producing methacrylic acid, comprising:

converting a C3-oxygenate into propanoic acid, wherein said C3-oxygenate is a compound selected from the group consisting of 1-propanol, monopropylene glycol, monohydroxyacetone, 2-hydroxypropanal, glycerol and dihydroxyacetone; and converting the propanoic acid into methacrylic acid.

BRIEF DESCRIPTION OF THE DRAWINGS

FIG. 1 shows a number of preparation routes starting from C3-oxygenates and resulting in propanoic acid.

DETAILED DESCRIPTION OF THE INVENTION

In the present invention, a C3-oxygenate is converted into methacrylic acid via propanoic acid as an intermediate.

In the final step of the present process, the propanoic acid is reacted with formaldehyde or a precursor of formaldehyde into methacrylic acid. A suitable example of a precursor of formaldehyde is methanol. The present process is illustrated in the following general reaction scheme wherein the starting material for the last step of the process is propanoic acid:

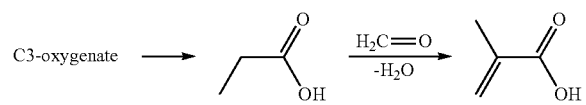

In the present process, the starting material is a C3-oxygenate. Within the present specification, a C3-oxygenate means a compound which contains 3 carbon atoms and 1, 2 or 3 oxygen atoms. The other atoms in such C3-oxygenate are hydrogen atoms. In the present process, the C3-oxygenate is not propanoic acid, because by C3-oxygenate reference is made herein only to the starting material of the present process.

An example of a C3-oxygenates containing 1 oxygen atom which may suitably be used in the present invention is 1-propanol.

Examples of C3-oxygenates containing 2 oxygen atoms which may suitably be used in the present invention are monopropylene glycol, monohydroxyacetone and 2-hydroxypropanal.

Examples of C3-oxygenates containing 3 oxygen atoms which may suitably be used in the present invention are glycerol, and dihydroxyacetone.

Preferably, in the present process, the C3-oxygenate contains 2 oxygen atoms. More preferably, such C3-oxygenate containing 2 oxygen atoms is monopropylene glycol, monohydroxyacetone or 2-hydroxypropanal, most preferably monopropylene glycol.

As discussed above, a disadvantage of the route for the production of methacrylic acid from acetone using hydrogen cyanide and sulfuric acid is that said route is accompanied by the undesired production of salts, such as ammonium sulfate, in large amounts. Further, as also discussed above, a disadvantage of the alternative route for the production of methacrylic acid by oxidation of isobutene is that two oxygen atoms have to be introduced into the isobutene by the use of an oxygen containing gas at high temperature (about 350° C.) and with release of a large amount of heat (about 600 kJ/mol). Further, as also discussed above, a further disadvantage for both said routes for the production of methacrylic acid is that non-renewable, fossil feedstocks have to be used, such as propene, propane and/or crude oil.

Surprisingly, with the integrated process of the present invention the above-mentioned disadvantages are avoided, while at the same time, advantageously, by means of the present invention C3-oxygenates, such as for example monopropylene glycol or glycerol, which may be formed as undesired (by)products in certain production processes such as biomass conversion processes, as discussed above, are valorized by transforming them into a chemical for which the worldwide demand is indeed high, namely methacrylic acid.

Preferably, in the present invention, the C3-oxygenates, for example monopropylene glycol and glycerol, originate from converting a renewable feedstock into such C3-oxygenates.

In the present invention, the C3-oxygenates, for example monopropylene glycol and glycerol, may originate from converting sugar sources, a renewable feedstock, such as sucrose, glucose, xylose or fructose, into such C3-oxygenates, for example by means of hydrogenolysis or hydrocracking of such sugar sources. These sugars may be used alone or in admixture. Further, these sugars may be present in monomeric, dimeric or polymeric form. Suitable polymeric sugars are cellulose, starch, inulin and hemicellulose.

For example, monoethylene glycol, monopropylene glycol and glycerol may be produced by the hydrogenolysis of one or more of the above-mentioned sugar sources. After separating the monopropylene glycol and glycerol from the monoethylene glycol, the monopropylene glycol and glycerol may advantageously be used as the C3-oxygenate in the present process. Such hydrogenolysis of sugar sources may be performed in any way, for example as described in above-mentioned "Hydrogenolysis Goes Bio: From Carbohydrates and Sugar Alcohols to Platform Chemicals" by Agnieszka M. Ruppert et al. in Angew. Chem. Int. Ed., 2012, 51, p. 2564-2601. Further reference is made to the above-mentioned disclosure of aqueous phase reforming of sugars by N. Li et al. in Journal of Catalysis, 2010, 270, p. 48-59. The disclosures of these publications are incorporated herein by reference.

Further, in a case where the C3-oxygenate is glycerol, the glycerol may also originate from converting triglycerides, a renewable feedstock, into glycerol, for example via esterification or hydrolysis of triglycerides.

In the present process wherein methacrylic acid is produced and wherein propanoic acid is an intermediate that is converted into methacrylic acid, the propanoic acid may be obtained from the C3-oxygenate in a variety of ways. In FIG. 1, a number of preparation routes starting from C3-oxygenates and resulting in propanoic acid are shown.

For a list of C3-oxygenates which may suitably be used in the present process wherein propanoic acid is an intermediate, reference is made to the above lists of C3-oxygenates containing 1, 2 or 3 oxygen atoms. Preferably, the C3-oxygenate contains 1 or 2 oxygen atoms, such as the C3-oxygenates as shown in FIG. 1 (excluding propanoic acid). More preferably, the C3-oxygenate contains 2 oxygen atoms. Most preferably, the C3-oxygenate is monopropylene glycol.

Preferably, in the present process, the C3-oxygenate is a C3-diol, in which case the process comprises:
converting the C3-diol into propanal;
converting the propanal into propanoic acid; and
reacting the propanoic acid with formaldehyde or a precursor of formaldehyde into methacrylic acid.

Said C3-diol contains 3 carbon atoms and 2 oxygen atoms in the form of 2 hydroxyl groups. The other atoms in such C3-diol are hydrogen atoms. In the present process, said C3-diol is preferably monopropylene glycol.

The reactions from the preparation routes in FIG. 1 may be carried out in ways as will be exemplified hereinbelow. The ways in which these reactions may be carried out are not essential to obtaining the above-discussed advantages of the present invention.

In FIG. 1, the designation "$-H_2$" refers to dehydrogenation in general. Such dehydrogenation may be either an endothermic dehydrogenation or an exothermic oxidative dehydrogenation wherein oxygen is added and water is released or a hydrogen transfer reaction. Therefore, in FIG. 1, the designation "−H$_2$" also covers "+0.5 O$_2$/−H$_2$O" (i.e. exothermic oxidative dehydrogenation) and hydrogen transfer, according to which H$_2$ is not released as H$_2$ or H$_2$O but as hydrogenated product such as alcohol (from a ketone) or alkane (from an olefin).

Further, in FIG. 1, the designation "+0.5 O$_2$" refers to oxidation in general. In some cases such as the oxidation of aldehydes to carboxylic acids, the desired conversion may also be achieved by adding water and release of hydrogen. Therefore, in FIG. 1, the designation "+0.5 O$_2$" may also cover "+H$_2$O/−H$_2$". The oxidation step may use oxidants such as H$_2$O$_2$, N$_2$O, peracids and other known organic and inorganic oxidants as well as electrochemical oxidation.

In general, there are the following types of reactions:
(1) reactions involving hydrogenation of a carbonyl group to a hydroxyl group;
(2) reactions involving dehydrogenation of a hydroxyl group to a carbonyl group or dehydrogenation of a carbonyl group to an α,β-unsaturated carbonyl group;
(3) reactions involving oxidation of an aldehyde group or a primary hydroxyl group to a carboxylic acid group;
(4) reactions involving dehydration of alcohols optionally followed by keto-enol rearrangement (e.g. monopropylene glycol to propanal or glycerol to 3-hydroxypropanal) or by hydrogenation of the resulting double carbon-carbon bond (glycerol to monopropylene glycol); and
(5) reactions involving hydroxyl-carbonyl isomerisation.

Reactions involving hydrogenation of a carbonyl group to a hydroxyl group as mentioned above under (1), may be carried out at a relatively low temperature, for example below 200° C., and a relatively high hydrogen pressure, for example higher than 10 bar. The catalyst may be a supported metal catalyst.

Reactions involving dehydrogenation of a hydroxyl group to a carbonyl group or dehydrogenation of a carbonyl group to an α,β-unsaturated carbonyl group as mentioned above under (2), may be carried out at a relatively high temperature, for example above 200° C., and a relatively low hydrogen pressure, for example lower than 1 bar. The catalyst may be a supported metal catalyst.

Reactions involving oxidation of an aldehyde group or a primary hydroxyl group to a carboxylic acid group as mentioned above under (3), may be carried out in the liquid phase at a relatively low temperature, for example at or below 200° C., in the presence of a base and an oxygen containing gas. The catalyst may be a supported metal catalyst, wherein the metal may be a noble metal, such as gold. Alternatively, it may be carried out in the gas phase at a relatively high temperature, for example of from 250 to 350° C., in the presence of an oxygen containing gas. The catalyst may be a mixed oxide that may be partly reduced under the reaction conditions.

Reactions involving dehydration of alcohols as mentioned above under (4), may be carried out in the gas phase at a relatively high temperature, for example at or above 150° C., suitably of from 150 to 400° C., using a solid acid and/or base catalyst. A keto-enol rearrangement may occur spontaneously over such catalysts. For a hydrogenation of the double carbon-carbon bond, the acid/base catalyst may also contain some hydrogenation activity. Such hydrogenation reaction may be carried out at a relatively high hydrogen pressure, for example higher than 10 bar.

Reactions involving hydroxyl-carbonyl isomerisation as mentioned above under (6), may be carried out using any catalyst at a relatively low temperature, for example higher than 100° C., and may even be carried in the absence of a catalyst at an elevated temperature.

In the table below, some publications are cited which disclose suitable reaction conditions for some of the reactions from the above general reaction scheme and from the reaction scheme in FIG. 1. The disclosures of these publications are incorporated herein by reference.

| Reaction | Publication |
|---|---|
| propanoic acid + formaldehyde or methanol → methacrylic acid | JP5331098A; JP63066146A; Industrial & Engineering Chemistry Research, 1997, 36, 11, p. 4600-4608 |
| monopropylene glycol → propanal | Appl. Catal. A: General, 2009, 366, p. 304-308; Appl. Catal. A: General, 2011, 400, p. 148-155 |
| 1-propanol → propanoic acid | ChemSusChem, 2012, 5, p. 2243-2248 |
| glycerol → monopropylene glycol | Chem. Commun., 2008, p. 6011-6012 |
| glycerol → dihydroxyacetone | Catal. Sci. Technol. 2012, 2, p. 1150 |

That which is claimed is:

1. A process for producing methacrylic acid, comprising:
converting a C3-oxygenate into propanoic acid, wherein said C3-oxygenate is a compound selected from the group consisting of 1-propanol, monopropylene glycol, monohydroxyacetone, 2-hydroxypropanal, glycerol and dihydroxyacetone; and
reacting the propanoic acid with formaldehyde or a precursor of formaldehyde into methacrylic acid, and wherein the C3-oxygenate originates from converting a renewable feedstock into the C3-oxygenate and the renewable feedstock is a sugar source.

2. A process according to claim 1, wherein the C3-oxygenate is selected from the group consisting of 1-propanol, monohydroxyacetone, 2-hydroxypropanal, glycerol and dihydroxyacetone.

3. A process according to claim 1, wherein the C3-oxygenate contains 2 oxygen atoms.

4. A process according to claim 3, wherein the C3-oxygenate containing 2 oxygen atoms is monopropylene glycol, monohydroxyacetone or 2-hydroxypropanal.

5. A process according to claim 4, wherein the C3-oxygenate is monopropylene glycol.

6. A process according to claim 1, wherein the sugar source is sucrose, glucose, xylose or fructose.

7. A process according to claim 1, wherein the C3-oxygenate is a C3-diol, comprising:
converting the C3-diol into propanal;
converting the propanal into propanoic acid; and
reacting the propanoic acid with formaldehyde into methacrylic acid.

* * * * *